United States Patent
Cedillo et al.

(10) Patent No.: US 9,701,708 B2
(45) Date of Patent: Jul. 11, 2017

(54) METHOD OF PREPARING OLIGOMERIC COMPOUNDS USING MODIFIED COUPLING PROTOCOLS

(71) Applicant: Ionis Pharmaceuticals, Inc., Carlsbad, CA (US)

(72) Inventors: Isaiah E. Cedillo, Vista, CA (US); Michael T. Migawa, Carlsbad, CA (US); W. Brad Wan, Fallbrook, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 14/764,655

(22) PCT Filed: Jan. 30, 2014

(86) PCT No.: PCT/US2014/013732
§ 371 (c)(1),
(2) Date: Jul. 30, 2015

(87) PCT Pub. No.: WO2014/120861
PCT Pub. Date: Aug. 7, 2014

(65) Prior Publication Data
US 2015/0368288 A1 Dec. 24, 2015

Related U.S. Application Data

(60) Provisional application No. 61/758,913, filed on Jan. 31, 2013.

(51) Int. Cl.
| | | |
|---|---|---|
| *C07H 21/00* | (2006.01) | |
| *C07H 21/02* | (2006.01) | |
| *C07H 1/00* | (2006.01) | |
| *C07H 19/06* | (2006.01) | |
| *C07H 19/16* | (2006.01) | |
| *C07H 1/02* | (2006.01) | |
| *C07H 1/04* | (2006.01) | |

(52) U.S. Cl.
CPC .............. *C07H 21/02* (2013.01); *C07H 1/00* (2013.01); *C07H 19/06* (2013.01); *C07H 19/16* (2013.01); *C07H 21/00* (2013.01); *C07H 1/02* (2013.01); *C07H 1/04* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,415,732 | A | 11/1983 | Caruthers et al. |
| 4,458,066 | A | 7/1984 | Caruthers et al. |
| 4,469,863 | A | 9/1984 | Ts'o et al. |
| 4,476,301 | A | 10/1984 | Imbach et al. |
| 4,500,707 | A | 2/1985 | Caruthers et al. |
| 4,668,777 | A | 5/1987 | Caruthers et al. |
| 4,725,677 | A | 2/1988 | Koster et al. |
| 4,973,679 | A | 11/1990 | Caruthers et al. |
| 4,981,957 | A | 1/1991 | Lebleu et al. |
| 5,023,243 | A | 6/1991 | Tullis |
| 5,034,506 | A | 7/1991 | Summerton et al. |
| 5,118,800 | A | 6/1992 | Smith et al. |
| 5,132,418 | A | 7/1992 | Caruthers et al. |
| RE34,069 | E | 9/1992 | Koster et al. |
| 5,166,315 | A | 11/1992 | Summerton et al. |
| 5,177,196 | A | 1/1993 | Meyer, Jr. et al. |
| 5,185,444 | A | 2/1993 | Summerton et al. |
| 5,188,897 | A | 2/1993 | Suhadolnik et al. |
| 5,194,599 | A | 3/1993 | Froehler |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |

(Continued)

FOREIGN PATENT DOCUMENTS

| | | |
|---|---|---|
| WO | WO 98/39352 | 9/1998 |
| WO | WO 99/14226 | 3/1999 |

(Continued)

OTHER PUBLICATIONS

Hudson et al. J. Am. Chem. Soc. (1993), vol. 115, pp. 2119-2124.*
Horn et al. Nucleic Acids Research (1989), vol. 17, pp. 6959-6967.*
Ravikumar et al. Organic Process Research & Development (2008), vol. 12, pp. 399-410.*
Xie et al. Organic Process Research & Development (2005), vol. 9, pp. 730-737.*
Brown et al., "Solid-phase oligonucleotide synthesis," (2011) http://www.atdbio.com/content/17/Solid-phase-oligonucleotide-synthesis#Activation-and-Coupling-Step-1 (retrieved on Jul. 25, 2016).
Pfundheller et al., "Locked nucleic acid synthesis," Quorum Sensing (2005) 288:127-145.
Seth et al., "Synthesis and Biophysical Evaluation 2', 4'-Constrained 2' O-Methoxyethyl and 2', 4'-Constrained 2' O-Ethyl Nucleic Analogues," The Journal of Organic Chemistry (2010) 75: 1569-1581.
Agrawal et al., "Protocols for Oligonucleotide Conjugates", Humana Press; New Jersey, 1994, 26, Ch 3.

(Continued)

*Primary Examiner* — Patrick Lewis
(74) *Attorney, Agent, or Firm* — Ionis Pharmaceuticals, Inc. Patent Dept.

(57) ABSTRACT

Provided herein are methods for the synthesis of oligomeric compounds wherein the standard coupling protocols are modified when coupling bicyclic nucleosides of Formula I. More particularly, the modified coupling protocols provide for a decrease in the ratio of phosphoramidite solution to activator solution in the coupling reagent with an increased contact time. The modified coupling protocols provide for oligomeric compounds having comparable yields to similar oligomeric compounds having modified nucleosides other than bicyclic nucleosides of Formula I.

15 Claims, No Drawings

(56) References Cited

U.S. PATENT DOCUMENTS

| | | | |
|---|---|---|---|
| 5,359,044 A | 10/1994 | Cook et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,489,677 A | 2/1996 | Sanghvi et al. |
| 5,514,785 A | 5/1996 | Van Ness et al. |
| 5,519,126 A | 5/1996 | Hecht |
| 5,519,134 A | 5/1996 | Acevedo et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,591,722 A | 1/1997 | Montgomery et al. |
| 5,596,086 A | 1/1997 | Matteucci |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,646,269 A | 7/1997 | Matteucci |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,700,920 A | 12/1997 | Altmann et al. |
| 5,721,218 A | 2/1998 | Froehler |
| 5,792,608 A | 8/1998 | Swaminathan et al. |
| 5,792,847 A | 8/1998 | Buhr et al. |
| 6,069,243 A * | 5/2000 | Scozzari ............ C07H 21/00 536/25.34 |
| 6,268,490 B1 | 7/2001 | Imanishi et al. |
| 6,525,191 B1 | 2/2003 | Ramasamy |
| 6,600,032 B1 | 7/2003 | Manoharan et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,867,294 B1 | 3/2005 | Sanghvi et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,547,684 B2 | 6/2009 | Seth et al. |
| 7,696,345 B2 | 4/2010 | Allerson et al. |
| 7,741,457 B2 | 6/2010 | Seth et al. |
| 8,278,283 B2 * | 10/2012 | Seth .................. C07H 21/00 514/42 |
| 2003/0176690 A1 | 9/2003 | Chatelain et al. |
| 2005/0130923 A1 | 6/2005 | Bhat et al. |
| 2005/0287555 A1 | 12/2005 | Dellinger et al. |
| 2005/0287566 A1 | 12/2005 | Wengel et al. |
| 2008/0015162 A1 * | 1/2008 | Bhanot ............ C12N 15/1137 514/44 A |
| 2008/0039618 A1 | 2/2008 | Allerson et al. |
| 2010/0234528 A1 | 9/2010 | Ravikumar et al. |
| 2011/0077390 A1 | 3/2011 | Seth et al. |
| 2011/0118454 A1 | 5/2011 | Peyrottes et al. |
| 2011/0130441 A1 | 6/2011 | Seth et al. |

FOREIGN PATENT DOCUMENTS

| | | |
|---|---|---|
| WO | WO 01/49687 | 7/2001 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036696 | 4/2010 |
| WO | WO 2010/036698 | 4/2010 |
| WO | WO 2011/017521 | 5/2011 |
| WO | WO 2011/115818 | 9/2011 |
| WO | WO 2011/139695 | 11/2011 |
| WO | WO 2011/139702 | 11/2011 |
| WO | WO 2011/156202 | 12/2011 |

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second-generation antisense oligonucleotides: structure—activity relationships and the design of improved signal-transduction inhibitors" Biochem. Soc. Trans. (1996) 24:630-637.

Altmann et al., "Second Generation of Antisense Oligonucleotides: From Nuclease Resistance to Biological Efficacy in Animals" Chimia. (1996) 50(4):168-176.

Altmann et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.

Alul et al., "Oxalyl-CPG: a labile support for synthesis of sensitive oligonucleotide derivatives" Nucleic Acid Research (1991) 19(7):1527.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bayer et al. "A new support for polypeptide synthesis in columns" Tetrahedron Letters (1970) 11(51):4503-4505.

Beaucage et al., "Deoxynucleoside Phosphoramidites—A New Class of Key Intermediates for Deoxypolynucleotide Synthesis" Tetrahedron Letters (1981) 22(20):1859-1862.

Beaucage et al., "Advances in the Synthesis of Oligonucleotides by the Phosphoramidite Approach" Tetrahedron (1992) 48(12):2223-2311.

Beaucage et al., "The Functionalization of Oligonucleotides Via Phosphoramidite Derivatives" Tetrahedron (1993) 49(10):1925-1963.

(56) References Cited

OTHER PUBLICATIONS

Beaucage et al., "The Synthesis of Specific Ribonucleotides and Unrelated Phosphorylated Biomolecules by the Phosphoramidite Method" Tetrahedron (1993) 49(46):10441-10488.
Bonora et al., "A Liquid-Phase Process Suitable for Large-Scale Synthesis of Phosphorothioate Oligonucleotides" Organic Process Research & Development (2000) 4:225-231.
Braasch et al., "Locked nucleic acid (LNA): fine-tuning the recognition of DNA and RNA" Chem. Biol. (2001) 8:1-7.
Elayadi et al., "Application of PNA and LNA oligomers to chemotherapy" Curr. Opinion Invens. Drugs (2001) 2:558-561.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003)31(21):6365-6372.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Gravert et al., "Organic Synthesis on Soluble Polymer Supports: Liquid-Phase Methodologies" Chem. Rev. (1997) 97(2):489-510.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Horvath et al., "Stereoselective synthesis of (−)-ara-cyclohexenyl-adenine" Tetrahedron Letters (2007) 48:3621-3623.
Jin et al., "Stereoselective Synthesis of Dithymidine Phosphorothioates Using Xylose Derivatives as Chiral Auxiliaries" J. Org. Chem. (1998) 63:3647-3654.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kumar et al., "The first analogues of LNA (locked nucleic acids): phosphorothioate-LNA and 2'-thio-LNA" Bioorg Med Chem Lett. (1998) 8:2219-2222.
Leumann et al., "DNA Analogues: From Supramolecular Principles to Biological Properties" Bioorganic & Medicinal Chemistry (2002) 10:841-854.
Martin, "Ein neuer Zugang zu 2'-O-Alkylribonucleosiden und Eigenschaften deren Oligonucleotide" Helv. Chim. Acta. (1995) 78(2):486-504.
McBride et al., "An Investigation of Several Deoxynucleoside Phosphoramidites Useful for Synethesizing Deoxyoligonucleotides" Tetrahedron Letters (1983) 24(3):245-248.
Nauwelaerts et al., "Cyclohexenyl nucleic acids: conformationally flexible oligonucleotides" Nucleic Acids Res. (2005) 33(8):2452-2463.
Nauwelaerts et al., "Structural characterization and biological evaluation of small interfering RNAs containing cyclohexenyl nucleosides" J. Am. Chem. Soc. (2007) 129(30):9340-9348.

Orum et al., "Locked nucleic acids: A promising molecular family for gene-function analysis and antisense drug development" Curr. Opinion Mol. Ther. (2001) 3:239-243.
Parr et al. "Solid-Phase Peptide Synthesis on an Inorganic Matrix having Organic Groups on the Surface" Chem. Internal. Ed. (1972) 11:314.
Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.
Robeyns et al., "Structure of the fully modified left-handed cyclohexene nucleic acid sequence GTGTACAC" J. Am. Chem. Soc. (2008) 130(6):1979-1984.
Scaringe, "RNA Oligonucleotide Synthesis via 5'-Silyl-2'-Orthoester Chemistry" Methods (2001) 23:206-217.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sinha et al., "Polymer support oligonucleotide synthesis XVIII: use of beta-cyanoethyl-N,N-dialkylamino/N-morpholino phosphoramidite of deoxynucleosides for the synthesis of DNA fragments simplifying deprotection and isolation of the final product" Nucleic Acid Research (1984) 12(11):4539-4557.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Verbeure et al., "RNase H mediated cleavage of RNA by cyclohexene nucleic acid (CeNA)" Nucleic Acids Res. (2001) 29(24):4941-4947.
Wahlestedt et al., "Potent and nontoxic antisense oligonucleotide containing locked nucleic acids" Proc. Natl. Acad. Sci. USA (2000) 97: 5633-5638.
Wang et al., "A stereoselective synthesis of dinucleotide phosphorothioate triesters through a chiral indo-loxazaphosphorine intermediate" Tetrahedron Letters (1997) 38(5):705-708.
Wang et al., "A stereoselective synthesis of dinucleotide phosphorothioates, using chiral indol-oxazaphosphorine intermediates" Tetrahedron Letters (1997) 38(22):3797-3800.
Wang et al., "A straightforward stereoselective synthesis of D- and L-5-hydroxy-4-hydroxymethyl-2-cyclohexenylguanine" J. Org. Chem. (2001) 66(25):8478-8482.
Wang et al., "Cyclohexene nucleic acids (CeNA) form stable duplexes with RNA and induce RNase H activity" Nucleosides Nucleotides Nucleic Acids (2001) 20(4-7):785-788.
Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.
Wang et al., "Stereocontrolled synthesis of ara-type cyclohexenyl nucleosides" J. Org. Chem. (2003) 68(11):4499-4505.
Wright et al. "Large scale synthesis of oligonucleotides via phosphoramidite nucleosides and a high-loaded polystyrene support" Tetrahedron Letters (1993) 34(21):3373-3376.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

* cited by examiner

METHOD OF PREPARING OLIGOMERIC COMPOUNDS USING MODIFIED COUPLING PROTOCOLS

SEQUENCE LISTING

The present application is being filed along with a Sequence Listing in electronic format. The Sequence Listing is provided as a file entitled DVCM0037USASEQ_ST.txt, created on Jul. 14, 2015 which is 4 Kb in size. The information in the electronic format of the sequence listing is incorporated herein by reference in its entirety.

FIELD OF THE INVENTION

The present disclosure is directed to the field of oligomer synthesis. In particular, improvements in the synthesis of oligomeric compounds are provided by modification of the coupling protocols during solid phase oligomer synthesis for bicyclic nucleosides having Formula I. In certain embodiments, the improvements in solid phase synthesis of oligomeric compounds include enhanced efficiency for the coupling of bicyclic nucleosides having Formula I. In certain embodiments, the modified coupling protocols provide improved yields.

BACKGROUND OF THE INVENTION

Oligonucleotides have been used in various biological and biochemical applications. They have been used as primers and probes for the polymerase chain reaction (PCR), as antisense agents used in target validation, drug discovery and development, as ribozymes, as aptamers, and as general stimulators of the immune system. This widespread use of oligonucleotides has led to an increasing demand for rapid, inexpensive and efficient methods for their synthesis.

Synthetic oligonucleotides are generally prepared through the repeated coupling of nucleoside phosphoramidites to 5'-hydroxyl groups of nucleoside monomers or the free 5'-hydroxyl groups of growing oligomers. A commonly used method to perform oligomer synthesis is the phosphoramidite approach (see for example: Beaucage and Caruthers (1981) Tetrahedron Letters 22:1859-1862; McBride and Caruthers (1983) Tetrahedron Letters 24:245-248; Sinha et al. (1984) Nucleic Acids Res. 12:4539-4557 and Beaucage and Iyer (1992) Tetrahedron 48:2223-2311, each of which is incorporated herein by reference in its entirety).

The synthesis of oligomeric compounds comprising one or more cEt bicyclic nucleosides (4'-CH(CH$_3$)—O-2' bridged nucleosides) has consistently provided lower yields than equivalent oligomeric compounds without cEt nucleosides. It was determined that cEt nucleosides were not coupling at the same efficiency as other modified nucleosides when using standard protocols wherein the coupling reagent is typically a 50/50 mixture of amidite solution and activator solution.

SUMMARY OF THE INVENTION

Provided herein are methods of preparing oligomeric compounds wherein the coupling protocols are modified for bicyclic nucleosides having Formula I. Such modified coupling protocols are particularly amenable to the automated large scale solid phase synthesis of oligomeric compounds using phosphoramidite monomer subunits. Use of the modified coupling protocols provides an improved coupling efficiency and overall yield while using the same number of equivalents of bicyclic nucleosides of Formula I as per standard protocols.

In certain embodiments, provided herein are methods of coupling solid support bound free hydroxyl groups to bicyclic nucleosides of Formula I:

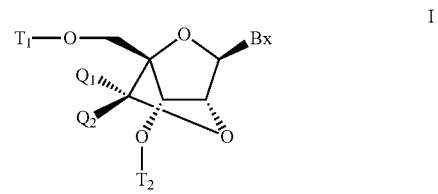

wherein for each bicyclic nucleoside of Formula I:
  Bx is an optionally protected heterocyclic base moiety;
  T$_1$ is a hydroxyl protecting group;
  T$_2$ is a reactive phosphorus group capable of forming an internucleoside linkage;
  one of Q$_1$ and Q$_2$ is H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl and the other of Q$_1$ and Q$_2$ is C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl;
  each substituted group is, independently, mono or poly substituted with substituent groups independently selected from halogen, OJ$_1$, SJ$_1$, NJ$_1$J$_2$, N$_3$, CN, C(=O)OJ$_1$, C(=O)NJ$_1$J$_2$, C(=O)J$_1$, O—C(=O)NJ$_1$J$_2$, N(H)C(=O)NJ$_1$J$_2$ and N(H)C(=S)NJ$_1$J$_2$;
  each J$_1$ and J$_2$ is, independently, H, C$_1$-C$_6$ alkyl, C$_2$-C$_6$ alkenyl, C$_2$-C$_6$ alkynyl, C$_1$-C$_6$ aminoalkyl or a protecting group;
  comprising treatment of the free hydroxyl groups with a coupling reagent which is about 70% by volume activator solution and about 30% by volume of a solution having about a 0.2 molar concentration of bicyclic nucleosides of Formula I and wherein the volume of coupling reagent added provides about 1.75 equivalents of bicyclic nucleosides of Formula I.

In certain embodiments, the 1.75 equivalents of bicyclic nucleosides of Formula I is based on the initial loading of the solid support with free hydroxyl groups.

In certain embodiments, the volume of coupling reagent added provides about 1.5 equivalents of bicyclic nucleosides of Formula I. In certain embodiments, the volume of coupling reagent added provides about 1.4 equivalents of bicyclic nucleosides of Formula I. In certain embodiments, the volume of coupling reagent added provides from about 1.75 to about 1.4 equivalents of bicyclic nucleosides of Formula I.

In certain embodiments, the flow rate is slowed down for addition of the coupling reagent to the solid support relative to standard protocols.

In certain embodiments, the recirculation time for the coupling reagent to the solid support is increased relative to standard protocols.

In certain embodiments, the activator solution comprises about 1.0 molar 4,5-dicyanoimidazole and about 0.1 molar N-methylimidazole in acetonitrile.

In certain embodiments, the solution of the bicyclic nucleosides of Formula I is prepared by dissolving the bicyclic nucleoside in either acetonitrile or a mixture of acetonitrile and toluene at about 50/50 (v/v) to provide a 0.2 molar solution.

In certain embodiments, the initial loading of the free hydroxyl groups on the solid support is greater than about 100 mmol. In certain embodiments, the initial loading of the free hydroxyl groups on the solid support is greater than about 200 mmol. In certain embodiments, the initial loading of the free hydroxyl groups on the solid support is from about 220 mmol to about 600 mmol. In certain embodiments, the initial loading of the free hydroxyl groups on the solid support is from about 220 mmol to about 900 mmol. In certain embodiments, the initial loading of the free hydroxyl groups on the solid support is greater than about 200 mmol and the delivery of the coupling reagent to the solid support is at a flow rate that requires from about 4 to about 5 minutes to deliver the about 1.75 equivalents. In certain embodiments, the initial loading of the free hydroxyl groups on the solid support is greater than about 200 mmol and the delivery of the coupling reagent to the solid support is at a flow rate that requires from about 4 to about 5 minutes to deliver the about 1.75 equivalents and further comprising recirculation of the coupling reagent for a time of from about 4.5 to about 5.5 minutes.

In certain embodiments, the free hydroxyl groups are bound to the solid support through linking moieties. In certain embodiments, the linking moieties are Unylinker™ groups. In certain embodiments, the free hydroxyl groups are located on monomer subunits that are linked directly or through a plurality of monomer subunits to the solid support.

In certain embodiments, each reactive phosphorus group is a diisopropylcyanoethoxy phosphoramidite. In certain embodiments, each $T_1$ is 4,4'-dimethoxytrityl.

In certain embodiments, $Q_1$ and $Q_2$ are each, independently, $C_1$-$C_6$ alkyl or substituted $C_1$-$C_6$ alkyl wherein each substituent group is $OJ_1$, $SJ_1$, $NJ_1J_2$, $N_3$ or CN and each $J_1$ and $J_2$ is, independently, H or $C_1$-$C_6$ alkyl. In certain embodiments, $Q_1$ and $Q_2$ are each $CH_3$. In certain embodiments, one of $Q_1$ and $Q_2$ is H and the other of $Q_1$ and $Q_2$ $C_1$-$C_6$ alkyl or substituted $C_1$-$C_6$ alkyl where the substituent group is each substituted group is $OJ_1$, $SJ_1$, $NJ_1J_2$, $N_3$ or CN wherein each $J_1$ and $J_2$ is, independently, H or $C_1$-$C_6$ alkyl. In certain embodiments, one of $Q_1$ and $Q_2$ is H and the other of $Q_1$ and $Q_2$ is $CH_3$.

In certain embodiments, each heterocyclic base moiety is, independently, an optionally protected purine, modified purine, pyrimidine or modified pyrimidine. In certain embodiments, each heterocyclic base moiety is, independently, uracil, thymine, cytosine, 4-N-benzoylcytosine, 4-N-benzoyl-5-methylcytosine, adenine, 6-N-benzoyladenine, guanine or 2-N-isobutyrylguanine.

In certain embodiments, provided herein are methods of large scale solid support synthesis of an oligomeric compound comprising a plurality of monomer subunits wherein at least one of the monomer subunits is a bicyclic nucleoside of Formula I:

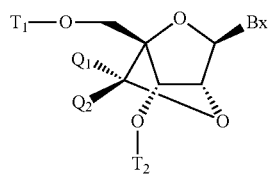

I wherein independently for each bicyclic nucleoside of Formula I:
  Bx is an optionally protected heterocyclic base moiety;
  $T_1$ is a hydroxyl protecting group;
  $T_2$ is a reactive phosphorus group capable of forming an internucleoside linkage;
  one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
  each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;
  each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
comprising the steps of:
  a) providing a solid support having a plurality of blocked hydroxyl groups attached thereto;
  b) deblocking the blocked hydroxyl groups to provide free hydroxyl groups;
  c) coupling monomer subunits to the free hydroxyl groups, wherein each monomer subunit comprises a phosphoramidite group and a blocked hydroxyl group to provide phosphite triester linked monomer subunits;
  d) oxidizing or sulfurizing the phosphite triester linked monomer subunits to provide phosphate triester or thiophosphate triester linked monomer subunits;
  e) optionally treating the phosphate triester or thiophosphate triester linked monomer subunits with a mixture of capping reagents to block any unreacted free hydroxyl groups;
  f) iteratively repeating steps b) through e) a predetermined number of times to provide the oligomeric compound; and
  wherein standard protocols are followed for each of the iterative steps except that the coupling step (step c) is modified for bicyclic nucleosides of Formula I such that coupling is performed using a coupling reagent comprising about 70% by volume activator solution and about 30% by volume of a solution having about a 0.2 molar concentration of bicyclic nucleosides of Formula I and wherein the volume of coupling reagent added provides from about 1.4 to about 1.75 equivalents of bicyclic nucleosides of Formula I based on the initial loading of the solid support and wherein the standard delivery flow rate of the coupling reagent to the solid support is reduced and the recirculation time of the coupling reagent to the solid support is increased.

In certain embodiments, the volume of coupling reagent added provides about 1.4 equivalents of bicyclic nucleosides of Formula I based on the initial loading of the solid support. In certain embodiments, the volume of coupling reagent added provides about 1.5 equivalents of bicyclic nucleosides of Formula I based on the initial loading of the solid support. In certain embodiments, the volume of coupling reagent added provides about 1.6 equivalents of bicyclic nucleosides of Formula I based on the initial loading of the solid support. In certain embodiments, the volume of coupling reagent added provides about 1.75 equivalents of bicyclic nucleosides of Formula I based on the initial loading of the solid support.

In certain embodiments, the activator solution comprises about 1.0 molar 4,5-dicyanoimidazole and about 0.1 molar N-methylimidazole in acetonitrile.

In certain embodiments, the solution of the bicyclic nucleosides of Formula I is prepared by dissolving the bicyclic nucleoside in either acetonitrile or a mixture of acetonitrile and toluene at about 50/50 (v/v) to provide a 0.2 molar solution.

In certain embodiments, the initial loading of the solid support is greater than about 100 mmol. In certain embodiments, the initial loading of the solid support is greater than about 200 mmol. In certain embodiments, the initial loading of the solid support is from about 220 mmol to about 900 mmol.

In certain embodiments, the initial loading of the solid support is greater than about 200 mmol and the delivery of the coupling reagent to the solid support is at a flow rate that requires from about 4 to about 5 minutes to deliver from about 1.4 to about 1.75 equivalents. In certain embodiments, the initial loading of the solid support is greater than about 200 mmol, the delivery of the coupling reagent to the solid support is at a flow rate that requires from about 4 to about 5 minutes to deliver from about 1.4 to about 1.75 equivalents and the recirculation of the coupling reagent is from about 4.5 to about 5.5 minutes. In certain embodiments, the initial loading of the solid support is greater than about 200 mmol, the delivery of the coupling reagent to the solid support is at a flow rate that requires from about 4 to about 5 minutes to deliver from about 1.4 to about 1.75 equivalents and the recirculation of the coupling reagent is from about 5 to about 10 minutes.

In certain embodiments, each reactive phosphorus group is a diisopropylcyanoethoxy phosphoramidite.

In certain embodiments, each $T_1$ is 4,4'-dimethoxytrityl.

In certain embodiments, $Q_1$ and $Q_2$ are each, independently, $C_1$-$C_6$ alkyl or substituted $C_1$-$C_6$ alkyl wherein each substituent group is $OJ_1$, $SJ_1$, $NJ_1J_2$, $N_3$ or CN and each $J_1$ and $J_2$ is, independently, H or $C_1$-$C_6$ alkyl. In certain embodiments, $Q_1$ and $Q_2$ are each $CH_3$. In certain embodiments, one of $Q_1$ and $Q_2$ is H and the other of $Q_1$ and $Q_2$ $C_1$-$C_6$ alkyl or substituted $C_1$-$C_6$ alkyl where the substituent group is each substituted group is $OJ_1$, $SJ_1$, $NJ_1J_2$, $N_3$ or CN wherein each $J_1$ and $J_2$ is, independently, H or $C_1$-$C_6$ alkyl. In certain embodiments, one of $Q_1$ and $Q_2$ is H and the other of $Q_1$ and $Q_2C_1$-$C_6$ alkyl or substituted $C_1$-$C_6$ alkyl where the substituent group is each substituted group is $OJ_1$, $SJ_1$, $NJ_1J_2$, $N_3$ or CN wherein each $J_1$ and $J_2$ is, independently, H or $C_1$-$C_6$ alkyl and the other of $Q_1$ and $Q_2$ is $CH_3$.

In certain embodiments, each heterocyclic base moiety is, independently, an optionally protected purine, modified purine, pyrimidine or modified pyrimidine. In certain embodiments, each heterocyclic base moiety is, independently, uracil, thymine, cytosine, 4-N-benzoylcytosine, 4-N-benzoyl-5-methylcytosine, adenine, 6-N-benzoyladenine, guanine or 2-N-isobutyrylguanine.

In certain embodiments, dichloroacetic acid in toluene is used to deblock blocked hydroxyl groups. In certain embodiments, dichloroacetic acid in toluene is used to deblock blocked hydroxyl groups and the oligomeric compound is further treated with triethylamine in acetonitrile to remove phosphorus protecting groups thereby providing linkages between monomer subunits that are independently selected from phosphodiester and phosphorothioate. In certain embodiments, dichloroacetic acid in toluene is used to deblock blocked hydroxyl groups, the oligomeric compound is then treated with triethylamine in acetonitrile to remove phosphorus protecting groups thereby providing linkages between monomer subunits that are independently selected from phosphodiester and phosphorothioate and then the oligomeric compound is treated with ammonium hydroxide to remove further protecting groups and cleave the oligomeric compound from the solid support.

DETAILED DESCRIPTION OF THE INVENTION

Provided herein are methods of preparing oligomeric compounds wherein the standard coupling protocols are modified for the coupling of bicyclic nucleosides having Formula I. Such modified coupling protocols are particularly amenable to automated large scale solid phase synthesis of oligomeric compounds using the phosphoramidite approach. Modifying the coupling protocol for bicyclic nucleosides of Formula I provide for more efficient coupling and improved yields.

In certain embodiments, the coupling reagent used in the modified coupling protocols comprises a much higher percentage of activator solution than phosphoramidite solution (about 70/30 as opposed to the standard 50/50). In certain embodiments, this requires an increased delivery time at about the same standard flow rate as for other phosphoramidites to deliver the standard 1.75 equivalents. The recirculation time is also modified to increase the contact time of the coupling reagent to the solid support.

In certain embodiments, the methods provided herein include coupling solid support bound free hydroxyl groups to bicyclic nucleosides of Formula I:

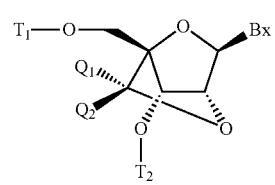

wherein for each bicyclic nucleoside of Formula I:

Bx is an optionally protected heterocyclic base moiety;

$T_1$ is a hydroxyl protecting group;

$T_2$ is a reactive phosphorus group capable of forming an internucleoside linkage;

one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each substituted group is, independently, mono or poly substituted with substituent groups independently selected from halogen, $OJ_1$, $SJ_1$, $NJ_1J_2$, $N_3$, CN, C(=O)$OJ_1$, C(=O)$NJ_1J_2$, C(=O)$J_1$, O—C(=O)$NJ_1J_2$, N(H)C(=O)$NJ_1J_2$ and N(H)C(=S)$NJ_1J_2$;

each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;

comprising treatment of the free hydroxyl groups with a coupling reagent which is about 70% by volume activator solution and about 30% by volume of a solution having about a 0.2 molar concentration of bicyclic nucleosides of Formula I and wherein the volume of coupling reagent added provides about 1.75 equivalents of bicyclic nucleosides of Formula I.

In certain embodiments, the methods provided herein include large scale solid support synthesis of an oligomeric compound comprising a plurality of monomer subunits wherein at least one of the monomer subunits is a bicyclic nucleoside of Formula I:

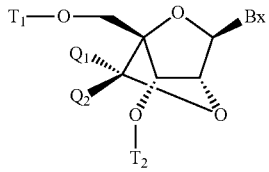

wherein independently for each bicyclic nucleoside of Formula I:
  Bx is an optionally protected heterocyclic base moiety;
  $T_1$ is a hydroxyl protecting group;
  $T_2$ is a reactive phosphorus group capable of forming an internucleoside linkage;
  one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
  each substituted group is, independently, mono or poly substituted with substituent groups independently selected from halogen, $OJ_1$, $SJ_1$, $NJ_1J_2$, $N_3$, CN, $C(=O)OJ_1$, $C(=O)NJ_1J_2$, $C(=O)J_1$, $O-C(=O)NJ_1J_2$, $N(H)C(=O)NJ_1J_2$ and $N(H)C(=S)NJ_1J_2$;
  each $J_1$ and $J_2$ is, independently, H, $C_1$-$C_6$ alkyl, $C_2$-$C_6$ alkenyl, $C_2$-$C_6$ alkynyl, $C_1$-$C_6$ aminoalkyl or a protecting group;
comprising the steps of:
  a) providing a solid support having a plurality of blocked hydroxyl groups attached thereto;
  b) deblocking the blocked hydroxyl groups to provide free hydroxyl groups;
  c) coupling monomer subunits to the free hydroxyl groups, wherein each monomer subunit comprises a phosphoramidite group and a blocked hydroxyl group to provide phosphite triester linked monomer subunits;
  d) oxidizing or sulfurizing the phosphite triester linked monomer subunits to provide phosphate triester or thiophosphate triester linked monomer subunits;
  e) optionally treating the phosphate triester or thiophosphate triester linked monomer subunits with a mixture of capping reagents to block any unreacted free hydroxyl groups;
  f) iteratively repeating steps b) through e) a predetermined number of times to provide the oligomeric compound; and
  wherein standard protocols are followed for each of the iterative steps except that the coupling step (step c) is modified for bicyclic nucleosides of Formula I such that coupling is performed using a coupling reagent comprising about 70% by volume activator solution and about 30% by volume of a solution having about a 0.2 molar concentration of bicyclic nucleosides of Formula I and wherein the volume of coupling reagent added provides about 1.75 equivalents of bicyclic nucleosides of Formula I based on the initial loading of the solid support and wherein the standard delivery flow rate of the coupling reagent to the solid support is reduced and the recirculation time of the coupling reagent to the solid support is increased.

The synthesis of oligomeric compounds is routinely performed using solution or solid phase chemistries. In solid phase oligonucleotide synthesis, oligonucleotides are assembled in a cyclical manner, each cycle consisting of a series of chemical reactions. Typically the first reaction is a deblocking reaction, i.e. the removal of a hydroxyl protecting group from a nucleoside monomer or an oligomer bound to a support. Generally, this requires the removal of a dimethoxytrityl protecting group to provide a free hydroxyl group (—OH). The next reaction is a coupling reaction, normally performed in the presence of an activator, wherein the free hydroxyl group is reacted with a nucleoside phosphoramidite to provide a phosphite triester. The next reaction is the oxidation or sulfurization of the phosphite triester to a phosphate triester or thiophosphate triester. The next reaction is the acetylation of unreacted free hydroxyl groups that failed to react with a phosphoramidite during the coupling cycle. This next step is referred to as the capping step and is performed using a mixture of capping reagents. Capping after the first phosphoramidite has been coupled is also effective in capping free hydroxyl and/or amino groups remaining on the solid support and free hydroxyl groups remaining on universal linker groups.

Provided herein are improved methods for the synthesis of oligomeric compounds comprising one or more bicyclic nucleosides of Formula I. The current standard for the synthesis of oligonucleotides is the phosphoramidite method utilizing phosphoramidites in an iterative process of coupling nucleoside phosphoramidites to 5'-hydroxyl groups of nucleoside monomers or growing oligomers that are attached to a solid support. This current standard method is also used to prepare oligomeric compounds wherein one or more of the nucleoside phosphoramidites is modified.

The loading of the solid support is typically calculated by trityl analysis. A small quantity of the solid support (~1 mg) is treated with a strong acid (e.g. a 1:1 mixture of concentrated HCl/EtOH) to cleave the DMT group. The absorbance at 495 nm of a sample of the resulting orange solution is measured in a UV/visible spectrophotometer. The amount of DMT cation is then calculated (extinction coefficient of DMT cation @ 495 nm, $E_{495}=71,700 M^{-1} cm^{-1}$; Loading (1 mg solid support)=$(E_{495}/A_{495} \times V \times (1/f))$.

The present methods are applicable to the preparation of oligomeric compounds comprising a wide range of monomer subunits such as nucleosides and modified nucleosides. In general each of the monomer subunits comprises a protected hydroxyl group and a phosphoramidite group. In certain embodiments, the hydroxyl protecting group is selected from substituted or unsubstituted trityl groups. In certain embodiments, the hydroxyl protecting group is 4,4'-dimethoxytrityl (DMT). In certain embodiments, the phosphoramidite group has the formula $-P(NR_2R_3)(OR_4)$, wherein $R_2$ and $R_3$ are each, independently, $C_1$-$C_6$ straight or branched alkyl, which includes but is not limited to, methyl, ethyl, n-propyl, 2-propyl, n-butyl, iso-butyl, and similar alkyl groups, and $R_4$ is any group that is compatible with oligonucleotide synthesis that may be removed after synthesis is complete. Preferably, $R_4$ is a substituted $C_1$-$C_6$ alkyl including at least one heteroatom. Most preferably, $R_4$ is —$CH_2CH_2CN$. A preferred phosphoramidite group is diisopropylcyanoethoxy phosphoramidite (—$P(N[(CH)CH_3]_2)(O(CH_2)_2CN)$).

In certain embodiments, methods of synthesizing of oligomeric compounds are provided that utilize support medium. In certain embodiments, reactive groups on the support medium are first functionalized with Unylinker™ linking groups prior to addition of the first monomer subunit. A first monomer subunit is attached to a support medium with subsequent monomer subunits iteratively coupled to provide a desired oligomeric compound. The industry standard for large scale oligomeric compound synthesis uses solid support media in a reaction vessel. The growing oligomeric compound is reacted and washed with various reagents and solvents while attached to the solid support. In certain embodiments, support media can be selected having variable solubility in different solvents to allow the growing support bound oligomeric compound to be either in or out of solution at various points in the synthesis process as desired. In certain embodiments, soluble supports include soluble polymer supports that allow precipitating and dissolving the iteratively synthesized product at desired points in the synthesis (Gravert et al., Chem. Rev., 1997, 97, 489-510).

The term "support media" is intended to include all forms of support, including those known to the art skilled for the synthesis of oligomeric compounds. Some representative support media that are amenable to the methods of the present invention include but are not limited to the following: crosslinked polystyrene (Primer Support 5G or Nitto-PhaseHL), controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support media, polyethylene glycol PEG's (see Bonora et al., Organic Process Research & Development, 2000, 4, 225-231).

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the term "alkoxy," refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein the term "aminoalkyl" refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "aralkyl" and "arylalkyl," refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein the term "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "heteroarylalkyl," refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethylene, pyrimidinylethylene, napthyridinylpropylene and the like. Heteroarylalkyl groups as used herein may optionally include further substituent groups on one or both of the heteroaryl or alkyl portions.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "mono or polycyclic ring system" is meant to include all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or polycyclic ring system can be further substituted with substituent groups such as for example phthalimide which has two =O groups attached to one of the rings. Mono or polycyclic ring systems can be attached to parent molecules using various strategies such as directly through a ring atom, fused through multiple ring atoms, through a substituent group or through a bifunctional linking moiety.

As used herein the terms "halo" and "halogen," refer to an atom selected from fluorine, chlorine, bromine and iodine.

As used herein the term "oxo" refers to the group (=O).

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxyl)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl) xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alky it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=N$R_{bb}$), amido (—C(O)N($R_{bb}$)($R_{cc}$) or —N($R_{bb}$)C(O)$R_{aa}$), azido (—N$_3$), nitro (—NO$_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein the term "nucleobase" generally refers to the nucleobase of a nucleoside or modified nucleoside. The term "heterocyclic base moiety" is broader than the term nucleobase in that it includes any heterocyclic base that can be attached to a sugar to prepare a nucleoside or modified nucleoside. In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines).

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH(CH$_3$)-4', 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system such as that used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each $R_p$, $R_q$ and $R_r$ is, independently, H, substituted or unsubstituted $C_1$-$C_{10}$ alkyl or a protecting group and where n and m are from 1 to about 10.

In certain embodiments, examples of sugar substituent groups include without limitation 2'-F, 2'-allyl, 2'-amino, 2'-azido, 2'-thio, 2'-O-allyl, 2'-OCF$_3$, 2'-O—$C_1$-$C_{10}$ alkyl, 2'-O—CH$_3$, OCF$_3$, 2'- O—CH$_2$CH$_3$, 2'-O—(CH$_2$)$_2$CH$_3$, 2'-O—(CH$_2$)$_2$—O—CH$_3$ (MOE), 2'-O(CH$_2$)$_2$SCH$_3$, 2'-O—CH$_2$—CH=CH$_2$, 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$) [N(R$_m$)(R$_n$)] wherein each $R_m$ and $R_n$ is, independently, H, substituted or unsubstituted $C_1$-$C_{10}$ alkyl or a protecting group. In certain embodiments, examples of 2,-sugar substituent groups include without limitation fluoro, —O—CH$_3$, —O—CH$_2$CH$_3$, —O—(CH$_2$)$_2$CH$_3$, —O—(CH$_2$)$_2$—O—CH$_3$, —O—CH$_2$—CH=CH$_2$, —O—(CH$_2$)$_3$—N(R$_1$)(R$_2$), O—(CH$_2$)$_2$—O—N(R$_1$)(R$_2$), —O—(CH$_2$)$_2$—O—(CH$_2$)$_2$—N(R$_1$)(R$_2$), —O—CH$_2$C(=O)—N(R$_1$)(R$_2$), —O—CH$_2$C(=O)—N(H)—(CH$_2$)$_2$—N(R$_1$)(R$_2$) and —O—CH$_2$—N(H)—C(=NR$_1$)[N(R$_1$)(R$_2$)] wherein $R_1$ and $R_2$ are each independently, H or $C_1$-$C_2$ alkyl. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$), —O—CH$_2$C(=O)—N(H)—(CH$_2$)$_2$—N(CH$_3$)$_2$ and —O—CH$_2$—N(H)—C(=NCH$_3$)[N(CH$_3$)$_2$]. In certain embodiments, examples of sugar substituent groups include without limitation fluoro, —O—CH$_3$, —O—(CH$_2$)$_2$—O—CH$_3$, —O—CH$_2$C(=O)—N(H)(CH$_3$) and —O—CH$_2$C(=O)—N(H)—(CH$_2$)$_2$—N(CH$_3$)$_2$. Further examples of modified sugar moieties include without limitation bicyclic sugars (e.g. bicyclic nucleic acids or bicyclic nucleosides discussed below).

In certain embodiments, examples of "sugar substituent group" or more generally "substituent group" include without limitation one or two 5'-sugar substituent groups independently selected from $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl and halogen. In certain embodiments, examples of sugar substituent groups include without limitation one or two 5'-sugar substituent groups independently selected from vinyl, 5'-methyl, 5'-(S)-methyl and 5'-(R)-methyl. In certain embodiments, examples of sugar substituent groups include without limitation one 5'-sugar substituent group selected from vinyl, 5'-(S)-methyl and 5'-(R)-methyl.

In certain embodiments, examples of sugar substituent groups include without limitation substituted silyl, an RNA cleaving group, a reporter group, an intercalator, a group for improving pharmacokinetic properties, or a group for improving the pharmacodynamic properties of an oligomeric compound, and other substituents having similar properties. In certain embodiments, oligomeric compounds include modified nucleosides comprising 2'-MOE substituent groups (Baker et al., *J. Biol. Chem.*, 1997, 272, 11944-12000). Such 2'-MOE substitution has been described as having improved binding affinity compared to unmodified nucleosides and to other modified nucleosides, such as 2'-O-methyl, 2'-O-propyl, and 2'-O-aminopropyl. Oligonucleotides having the 2'-MOE substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

Sugar moieties can be substituted with more than one sugar substituent group including without limitation 2'-F-5'-methyl substituted nucleosides (see PCT International Application WO 2008/101157, published on Aug. 21, 2008 for other disclosed 5',2'-bis substituted nucleosides). Other combinations are also possible, including without limitation, replacement of the ribosyl ring oxygen atom with S and further substitution at the 2'-position (see published U.S. Patent Application US2005-0130923, published on Jun. 16, 2005) and 5'-substitution of a bicyclic nucleoside (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates. As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH(CH$_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms. Examples of such 4' to 2' bridged bicyclic nucleosides, include but are not limited to one of formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-C—H (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N (OCH$_3$)-2' (and analogs thereof see published International Application WO2008/150729, published Dec. 11, 2008); 4'-CH$_2$—O—N(CH$_3$)-2' (see U.S. Pat. No. 796,345, issued on Apr. 13, 2010,); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C—(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication Nos.: US2008-0039618; U.S. Patent Application Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic nucleosides comprise a bridge between the 4' and the 2' carbon atoms of the pentofuranosyl sugar moiety including without limitation, bridges comprising 1 or from 1 to 4 linked groups (generally forming a 4 to 6 membered ring with the parent sugar moiety) independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, 5J$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'—CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiments, bicyclic nucleosides have the formula:

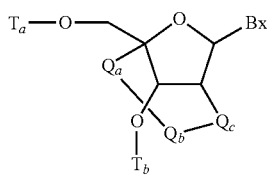

wherein:
Bx is a heterocyclic base moiety;
-Q$_a$-Q$_b$-Q$_c$- is —CH$_2$—N(R$_c$)—CH$_2$—, —C(=O)—N(R$_c$)—CH$_2$—, —CH$_2$—O—N(R$_c$)—, —CH$_2$—N(R$_c$)—O— or —N(R$_c$)—O—CH$_2$;
R$_c$ is C$_1$-C$_{12}$ alkyl or an amino protecting group; and
T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

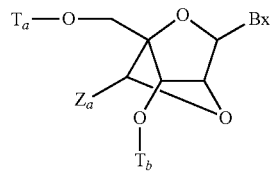

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_a$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, OJ$_c$, NJ$_c$J$_d$, SJ$_c$, N$_3$, OC(=X)J$_c$, and NJ$_e$C(=X)NJ$_c$J$_d$, wherein each J$_c$, J$_d$ and J$_e$ is, independently, H, C$_1$-C$_6$ alkyl, or substituted C$_1$-C$_6$ alkyl and X is O or NJ$_c$.

In certain embodiments, bicyclic nucleosides have the formula:

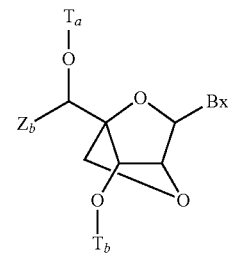

wherein:
Bx is a heterocyclic base moiety;
T$_a$ and T$_b$ are each, independently H, a hydroxyl protecting group, a conjugate group, a reactive phosphorus group, a phosphorus moiety or a covalent attachment to a support medium;
Z$_b$ is C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl, substituted C$_2$-C$_6$ alkynyl or substituted acyl (C(=O)—).

In certain embodiments, bicyclic nucleosides have the formula:

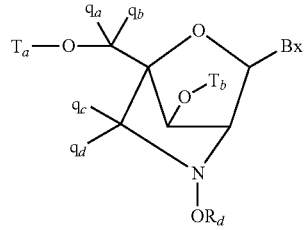

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

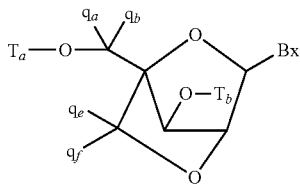

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$J_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

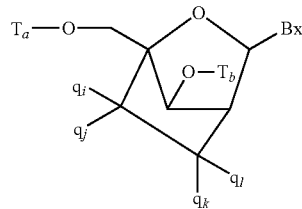

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$J_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-$CH_2$—O-2') BNA (B) β-D-methyleneoxy (4'-$CH_2$—O-2') BNA (C) ethyleneoxy (4'-($CH_2$)$_2$—O-2') BNA (D) aminooxy (4'-$CH_2$—O—N(R)-2') BNA, (E) oxyamino (4'-$CH_2$—N(R)—O-2') BNA, (F) methyl(methyleneoxy) (4'-CH($CH_3$)—O-2') BNA (also referred to as constrained ethyl or cEt), (G) methylenethio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, (J) propylene carbocyclic (4'-($CH_2$)$_3$-2') BNA, and (K) vinyl BNA as depicted below.

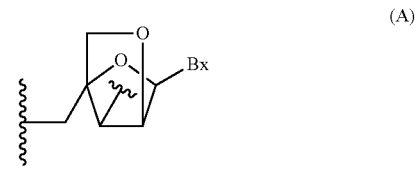

(A)

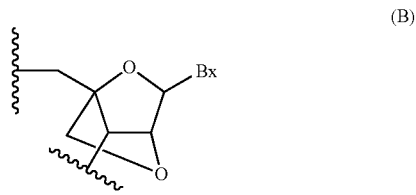

(B)

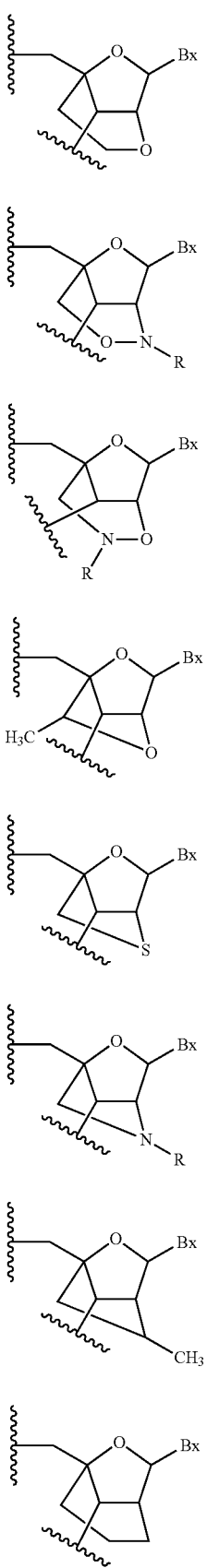

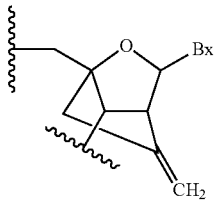

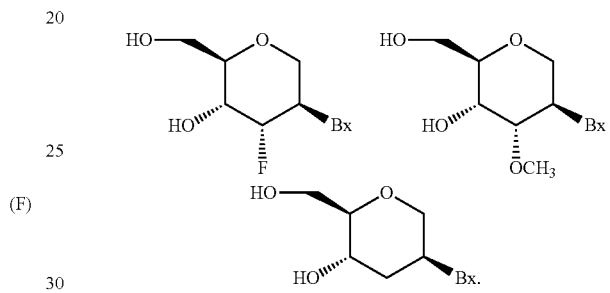

wherein Bx is the base moiety and R is, independently, H, a protecting group, $C_1$-$C_6$ alkyl or $C_1$-$C_6$ alkoxy.

In certain embodiments, modified nucleosides include nucleosides having sugar surrogate groups that include without limitation, replacement of the ribosyl ring with a sugar surrogate such as a tetrahydropyranyl ring system (also referred to as hexitol) as illustrated below:

In certain embodiments, sugar surrogates are selected having the formula:

wherein:
Bx is a heterocyclic base moiety;
one of $T_3$ and $T_4$ is an internucleoside linking group attaching the tetrahydropyran nucleoside analog to the remainder of one of the 5' or 3' end of the oligomeric compound and the other of $T_3$ and $T_4$ is hydroxyl, a protected hydroxyl, a 5' or 3' terminal group or an internucleoside linking group attaching the tetrahydropyran nucleoside analog to the remainder of the other of the 5' or 3' end of the oligomeric compound;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

Such sugar surrogates can be referred to as a "modified tetrahydropyran nucleoside" or "modified THP nucleoside". Modified THP nucleosides include, but are not limited to, what is referred to in the art as hexitol nucleic acid (HNA), altritol nucleic acid (ANA), and mannitol nucleic acid (MNA) (see Leumann, C. J., *Bioorg. & Med. Chem.*, 2002, 10, 841-854).

In certain embodiments, oligomeric compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., *J. Am. Chem. Soc.*, 2007, 129(30), 9340-9348; Gu et al., *Nucleosides, Nucleotides & Nucleic Acids*, 2005, 24(5-7), 993-998; Nauwelaerts et al., *Nucleic Acids Research*, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., Nucleic Acids Research, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

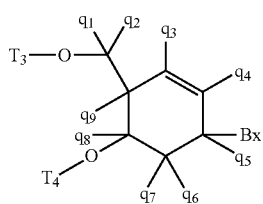

X wherein independently for each of said at least one cyclohexenyl nucleoside analog of Formula X:

Bx is a heterocyclic base moiety;

one of $T_3$ and $T_4$ is an internucleoside linking group attaching the cyclohexenyl nucleoside to the remainder of one of the 5' or 3' end of the oligomeric compound and the other of $T_3$ and $T_4$ is hydroxyl, a protected hydroxyl, a 5' or 3' terminal group or an internucleoside linking group attaching the cyclohexenyl nucleoside to the remainder of the other of the 5' or 3' end of the oligomeric compound; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

Some representative U.S. patents that teach the preparation of such modified sugars include without limitation, U.S. Pat Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein the term "reactive phosphorus" is meant to include groups that are covalently linked to a monomer subunit that can be further attached to an oligomeric compound that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH(CH$_3$)$_2$]$_2$]O(CH$_2$)$_2$CN) and H-phosphonate (—O*—P(=O)(H)OH), wherein the O* is normally attached to the 3'-position of the Markush group of Formula I. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Chiral auxiliaries are known in the art (see for example: Wang et al., *Tetrahedron Letters*, 1997, 38(5), 705-708; Jin et al., *J. Org. Chem*, 1997, 63, 3647-3654; Wang et al., *Tetrahedron Letters*, 1997, 38(22), 3797-3800; and U.S. Pat. No. 6,867,294, issued Mar. 15, 2005). Additional reactive phosphates and phosphites are disclosed in Tetrahedron Report Number 309 (Beaucage and Iyer, *Tetrahedron*, 1992, 48, 2223-2311).

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

As used herein, the term "oligomeric compound" refers to a contiguous sequence of linked monomer subunits. Each linked monomer subunit normally includes a heterocyclic base moiety but monomer subunits also includes those without a heterocyclic base moiety such as abasic monomer subunits. In certain embodiments, at least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. : 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, the steps for large scale synthesis of oligomeric compounds, other than coupling steps with bicyclic nucleosides of Formula I, are performed in accordance with published literature (see for example, Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA: Protein Interactions*, Smith, Ed., 1998, 1-36; Gallo et al., *Tetrahedron*, 2001, 57, 5707-5713; Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069).

Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O[1(2-fluorophenyl)-4-methoxypiperidin-4-yl] (FPMP), 2'-O-[(triisopropylsilypoxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy) methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilypoxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

All documents, or portions of documents, cited in this application, including, but not limited to, patents, patent applications, articles, books, and treatises, are hereby expressly incorporated by reference in their entirety for any purpose.

Those skilled in the art, having possession of the present disclosure will be able to prepare oligomeric compounds, comprising a contiguous sequence of linked monomer subunits, of essentially any viable length. While in certain embodiments, oligomeric compounds provided herein can be prepared as described, the following examples serve only to illustrate and are not intended to be limiting.

EXAMPLE 1

Unylinker™ Functionalized Support Medium

Solid support material, Primer Support 5G or NittoPhase-HL, functionalized with universal linking groups (Unylinker™) is commercially available from H.C. Brown Pharmaceutical Research and Laboratories. Unylinker™ and macroporous aminomethyl resin are also commercially available separately from Tianjin Nankai Hecheng Science and Technology Company, Ltd.

EXAMPLE 2

Preparation of Solutions Used for the Synthesis of Oligomeric Compounds

Unless otherwise stated, solvents have water content less than 100 ppm as determined by Karl Fischer titrimetry. The concentrations of reagents listed herein and the solvents utilized are typical and not meant to be limiting.

The detritylation solution is typically prepared in a 1:9 volumetric ratio of dichloroacetic acid (DCA) to toluene. The volumetric ratio of DCA to toluene can also be varied. The detritylation solution is prepared in the lab or special ordered from either Tedia or EMD Chemicals. The detritylation solution is used in the detritylation step "B" for deprotecting the 4, 4'-Dimethoxytrityl (5'-DMT) groups.

The 0.2 M amidite solutions are typically prepared in the lab by adding the solid amidite directly into an appropriately filled dedicated reservoir with acetonitrile (ACN). Toluene has also been used for making the 0.2 M amidite solutions. When preparing 0.2 M cEt amidite solutions (4'-CH(CH$_3$)—O-2' bridged BNAs) a 1:1 mixture of acetonitrile and toluene is used sometimes used for 5-methylcytosine cEt phosphoramidite and usually used for cEt guanidine phosphoramidite. Other 0.2 M cEt amidite solutions are routinely prepared in acetonitrile but may also be prepared in a 1:1 mixture of acetonitrile and toluene. The activator solution is typically prepared in the lab by adding the solid 4, 5-dicyanoimidazole (DCI) and liquid N-methylimidazole (NMI) directly into an appropriate filled reservoir with acetonitrile mixture to have a final concentration of 1.0 M DCI and 0.1 M NMI. The concentrations of phosphoramidite, DCI and NMI can also be varied. The selected phosphoramidite solution is automatically mixed with the activator solution in a 1:1 volumetric ratio by an automated synthesizer to create the coupling solution. This volumetric ratio is adjusted to about 70/30 when coupling cEt phosphoramidite solutions wherein the 70% is the activator solution. The coupling solution is used in the coupling step "D" to add 5'-DMT phosphoramidite monomer subunits.

Typical phosphoramidite solutions include without limitation: 5'-DMT-2'-deoxyadenosine phosphoramidite (0.2 M, dA amidite); 5'-DMT-2'-deoxycytosine phosphoramidite (0.2 M, dC amidite), 5'-DMT-2'-deoxy-5-methylcytosine phosphoramidite (0.2 M, d$^{Me}$C amidite), 5'-DMT-2'-deoxyguanosine phosphoramidite (0.2 M, dG amidite), 5'-DMT-2'-deoxythymidine phosphoramidite (0.2 M, dT amidite), 5'-DMT-2'-O(CH$_2$)$_2$—OCH$_3$ adenosine phosphoramidite (0.2 M, 2'-MOE A amidite); 5'-DMT-2'-O(CH$_2$)$_2$—OCH$_3$ 5-methylcytosine phosphoramidite (0.2 M, 2'-MOE $^{Me}$C amidite); 5'-DMT-2'-O(CH$_2$)$_2$—OCH$_3$ guanosine phosphoramidite (0.2 M, 2'-MOE G amidite) and 5'-DMT-2'-O(CH$_2$)$_2$—OCH$_3$ 5-methyluridine phosphoramidite (0.2 M, 2'-MOE $^{Me}$U amidite), 5'-DMT-2',4'-0(CHCH$_3$) adenosine phosphoramidite (0.2 M, cEt A amidite), 5'-DMT-2',4'-0 (CHCH$_3$) 5-methylcytosine phosphoramidite (0.2 M, cEt $^{Me}$C amidite); 5'-DMT-2',4'-0(CHCH$_3$)-guanosine phosphoramidite (0.2 M, cEt G amidite) and 5'-DMT-2',4'-O (CHCH$_3$) 5-methyluridine phosphoramidite (0.2 M, cEt $^{Me}$U (T) amidite). Phosphoramidites can be prepared to have a desired stereochemistry such as 6'-(R) or (S)—CH$_3$ cEt phosphoramidites. The phosphoramidite heterocyclic bases that have exocyclic amino groups are normally prepared with amino protecting groups such as 4-N-benzoylcytosine, 4-N-benzoyl-5-methylcytosine, 6-N-benzoyladenine or 2-N-isobutyrylguanine. The 0.2 M phenylacetyl disulfide (PADS) sulfurization solution is typically prepared in the lab by adding the solid reagent directly to an appropriate reservoir filled with equal volumes of acetonitrile and 3-picoline (3-PIC). The concentration of PADS and volumetric ratio of ACN to 3-PIC can also be varied. Once the PADS solution is completely mixed it is then allowed to age 12 hours prior to use in the synthesis sulfurization step "F".

The solutions used for capping can vary in compositions and reagents but invariably deliver an excess of equivalents of acetic anhydride to unreacted sites to block them from further reaction. One solution for capping consists of Capping Reagent A (2/3/5 volumetric mix of N-methylimidazole/pyridine/toluene) and Capping Reagent B (1/4 volumetric mix of acetic anhydride in toluene). The volumetric ratio of NMI, pyridine and toluene for Capping Reagent A and the volumetric ratio of acetic anhydride and toluene for Capping Reagent B can also be varied. Capping Reagent A and Capping Reagent B are prepared in the lab or special ordered from either Tedia or EMD Chemicals. A solution of Capping Reagent A is automatically mixed with a solution of Capping Reagent B in a 1:1 volumetric ratio by an automated synthesizer to create the capping solution (mixture of capping reagents). The capping solution is used in the capping step "H" for capping (acetylation) of any uncoupled free hydroxyl groups due to incomplete coupling.

The phosphorus deprotection solution is typically prepared in a 1:1 volumetric ratio of triethylamine/acetonitrile. The phosphorus deprotection solution is typically prepared in the lab. The volumetric ratio of triethylamine and ACN can also be varied. The phosphorus deprotection solution is used in the phosphorus deprotection step "J" for deprotecting the phosphorus protecting groups.

EXAMPLE 3

General Synthetic Steps for Oligonucleotide Synthesis

In certain embodiments, the synthetic steps and reagents used in oligomeric compound synthesis are as shown below:

| Synthesis Step | Synthesis Solution | Reagent/Solvent |
| --- | --- | --- |
| A | Column Packing | Primer Support 5G or NittoPhase-HL solid support slurried in Acetonitrile |
| B | Detritylation | Dichloroacetic Acid/Toluene (1:9, v/v) |
| C | Detritylation Rinse | Toluene or Acetonitrile |
| D | Coupling | 0.2M Amidite in Acetonitrile |
|   | Coupling Activator | 1.0M 4,5-Dicyanoimidazole with 0.1M N-methylimidazole in Acetonitrile |
| E | Coupling Rinse | Acetonitrile |
| F | Sulfurization | 0.2M Phenylacetyl Disulfide in Acetonitrile/3-Picoline (1:1, v/v) aged ≥12 hours |
| G | Sulfurization Rinse | Acetonitrile |
| H | Capping A | N-methylimidazole/Pyridine/Toluene (2:3:5, v/v/v) |
|   | Capping B | Acetic Anhydride/Toluene (1:4, v/v) |
| I | Capping Rinse | Toluene or Acetonitrile |
| J | Phosphorus Deprotection | Triethylamine/Acetonitrile (1:1, v/v) |
| K | End Wash | Toluene or Acetonitrile. |

Those skilled in the art would realize that many of the reagents and or solvents can be modified or substituted from that listed above while providing comparable results. Such modified reagents are known in the art. In certain embodiments, automated synthesis is performed as per the above steps with modification or substitution of one or more of the solid support material, detritylation reagents, rinse or wash solvents, activator reagents, amidite solution, sulfurization reagent, capping reagents (A and or B) or deprotection reagents. In general, the equivalents are essentially the same for each modified synthesis wherein the main differences are in the solvents and or types of reagents used such as for example differences in capping reagents (5% to about 10% acetic anhydride, from about 5% to about 10% N-methylimidazole and from about 5% to about 15% pyridine or from about 5% to about 10% 2,6-lutidine dissolved in tetrahydrofuran, toluene or acetonitrile). Other examples include different types of sulfurizing reagents available and or replacement of the sulfurization reagent which produces a phosphorothioate internucleoside linkage with an oxidizing reagent to produce a phosphodiester linkage.

EXAMPLE 4

General Method for Solid Phase Synthesis of Oligomeric Compounds

In certain embodiments, general methods for preparing oligomeric compounds on a solid phase medium is performed as outlined below:

a) providing a synthesis column packed with a solid support having a plurality of blocked hydroxyl groups;

b) contacting the solid support with a deblocking solution to provide free hydroxyl groups;

c) contacting the solid phase with one or more solvents to wash the solid phase;

d) contacting the solid phase with a coupling mixture by simultaneously contacting the solid phase with equal volumes of a solution containing a selected monomer subunit capable of forming a phosphite intermediate and a solution containing an activator;

e) recontacting the solid phase with the coupling mixture one or more times by recirculating the coupling mixture through a recirculation loop;

f) contacting the solid phase with one or more solvents to wash the solid phase;

g) contacting the solid phase with an oxidizing or sulfurizing solution;

i) contacting the solid phase with one or more solvents to wash the solid phase;

j) contacting the solid phase with a capping mixture by simultaneously contacting the solid phase with equal volumes of a solution containing a acetic anhydride and a solution containing a base such as dicyanoimidazole;

k) contacting the solid phase with one or more solvents to wash the solid phase;

l) repeating steps b) through k) to prepare the oligomeric compound.

To obtain the purified oligomeric compound the support bound fully protected oligomeric compound is generally base deprotected and cleaved from the solid support by heating and treating with a solution of ammonium hydroxide. The DMT on product is then generally purified by reverse phase column chromatography. Further purification can be performed by several methods such as precipitation. Detritylation is generally performed using glacial acetic acid.

EXAMPLE 5

Study to Optimize Coupling Protocols for cEt Phosphoramidites (2.0 mmol scale)

Synthesis of 3/10/3 gapped oligonucleotides (SEQ ID NO: 01) was performed on a GE Healthcare AKTA OligoPilot Plus 100 synthesizer in a FineLINE 35 mm column at 2.0 mmol scale using the procedures set forth below. The synthesis was performed utilizing standard coupling protocols for deoxy and MOE phosphoramidites. The standard coupling protocols were modified for the cEt coupling step such that one or more of the molar equivalents of cEt phosphoramidite delivered, the delivery time and the recirculation time were modified during the coupling step in an effort to improve cEt coupling efficiency. Standard coupling protocols for a 2.0 mmol scale run are listed below (coupling reagent 70.0 mL (0.2M phosphoramidite solution 35.0 mL simultaneously delivered with activator 35.0 mL): delivery flow rate of coupling reagent 35.0 mL/min; delivery time 2.0 min; recirculation time 3.0 min (35.0 mL/min for 1.2 min. then 70.0 mL/min for 1.8 min).

Two mmol of VIMAD Unylinker™ (Uny) solid support was weighed into the synthesis column and slurried in acetonitrile. The piston was lowered to 6.3 cm as measured by calipers with excess ACN directed through the top inlet of the column. This packing equated to 9.6 mL of column volume per gram of solid support. Dichloroacetic acid (10%) in toluene was used for deblocking of DMT groups. DCI (1.0 M) in the presence of NMI (0.1 M) was used as activator during the coupling step. Activator and phosphoramidite (0.2 M) solutions were delivered simultaneously during the coupling step. PADS (phenylacetyl disulfide, 0.2 M) in 3-picoline and ACN (1:1, v/v) was used as sulfur transfer reagent. Capping reagents used to cap unreacted hydroxyls were cap A: 1:4 $AC_2O$ toluene (v/v) and cap B: 2:3:5 NMI/pyridine/toluene (v/v/v). At the end of the synthesis, the support-bound DMT-on oligonucleotide was treated with a solution of TEA in ACN (1:1, v/v) to remove acrylonitrile formed by deprotection of cyanoethyl group from phosphorothioate triester. The synthesis and reagents are presented in Table 1. The reaction parameters are presented in Table 2.

TABLE 1

Reagents and solvents used for solid-phase oligonucleotide synthesis

| Synthesis Step | Reagent/Solvent |
| --- | --- |
| Detritylation | 10% DCA in toluene |
| Coupling | 0.2M cEt $^{Me}$C phosphoramidite ACN/toluene (1:1, v/v) |
| | 0.2M other phosphoramidites in ACN |
| Coupling Activation | 1.0M DCI with 0.1M NMI in ACN |
| Sulfurization | 0.2M PADS in ACN/3-picoline (1:1, v/v) |
| Capping A | NMI/pyridine/toluene (2:3:5, v/v/v) |
| Capping B | Acetic Anhydride/Toluene (1:4, v/v) |
| Phosphorous Deprotection | TEA in ACN (1:1, v/v) |
| Cycle End Wash | Toluene |
| Rinses & Washes | ACN. |

TABLE 2

Standard oligonucleotide synthesis protocol (2.0 mmol)

| Synthesis Step | Cycle | Volume (mL) | Flow Rate (mL/min) | Delivery (min) | Recirculation (min) |
| --- | --- | --- | --- | --- | --- |
| Detritylation | 1 (Uny) | 178.34 | 46.40 | 3.5 | |
| | 2-16 | 127.34 | 46.40 | 2.5 | |
| Coupling | | | | | |
| Amidites | 2-16 | 17.0 | 8.5[1] | (MOE and deoxy, see Table 3 for cEt) | |
| Activator | 2-16 | 17.0 | 8.5[1] | | |
| Coupling reagent total volumes/times | | 35.0 | 17.5 | 2.0 | 3.0[2] |
| Sulfurization | 1-16 | 64.82 | 20.30 | 3.2 | |
| Capping | 1 (Uny) | 162.08 | 21.6[3] | 7.5 | 7.5[4] |
| (Reagent A/B) | 2-15 | 32.42 | 21.6[3] | 1.5 | |
| Phosphorus Deprotection | NA | 92.6 | 46.4 | 2.0 | 120 |

[1]Phosphoramidite and activator solutions were delivered simultaneously, 50/50, %/% (v/v)
[2]Following delivery, coupling reagent is recirculated 17.6 mL/min for 1.2 min. then 35.2 mL/min for 1.8 min.
[3]Capping A and capping B solutions were delivered simultaneously, 50/50, %/% (v/v)
[4]Following delivery, reagents were recirculated at 21.6 mL/min/mmol for 7.5 min.

It was determined that coupling efficiency for cEt phosphoramidites was lower than for other phosphoramidites using the standard coupling conditions in oligonucleotide synthesis. Following standard coupling protocols, a volume of phosphoramidite solution is delivered for each coupling that provides about 1.75 equivalents of phosphoramidite. Initially, an increased amount of cEt phosphoramidites and overall reaction time (i.e. delivery time plus recirculation time) were used in small scale experiments to improve the yield to what would be expected when using non-cEt amidites. However, this approach would result in having to use large amounts of cEt amidites relative to other amidites for large scale oligo synthesis. To optimize the coupling efficiency of cEt phosphoramidites, a series of oligomeric compounds were prepared using standard coupling protocols for all amidites except for cEt amidites. The maximize the coupling efficiency for cEt phosphoramidites the standard coupling protocols were adjusted by varying one or more of the phosphoramidite equivalents, coupling activation, delivery time and recirculation time during the coupling step.

| SEQ ID NO./ ISIS NO. | Composition (5' to 3') |
| --- | --- |
| 01/481464 | $^{Me}C_kT_kA_k$TTTGGATGT$^{Me}CA_kG_k^{Me}C_k$ |
| 01/518349 | $^{Me}C_eT_eA_e$TTTGGATGT$^{Me}CA_kG_k^{Me}C_k$ |

Each internucleoside linkage is a phosphorothioate and each nucleoside not followed by a subscript e or k is a β-D-2'-deoxyribonucleoside. Each $^{Me}$C is a 5-methyl cytosine modified nucleoside. Each nucleoside followed by a subscript "e" is a 2'-O-methoxyethyl (MOE) modified nucleoside. Each nucleoside followed by a subscript "k" is a bicyclic nucleoside having a 4'-CH((S)—CH$_3$)—O-2' bridge also referred to as a (S)-cEt modified nucleoside.

Nucleosides followed by subscripts "e" or "k" are further illustrated below.

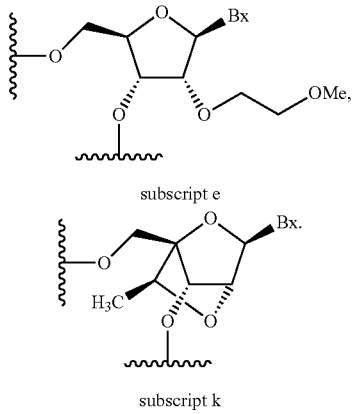

subscript e subscript k

TABLE 3 cEt phosphoramidite coupling conditions used for Example 5

| Run | SEQ ID NO./ ISIS NO. | Activator/ amidite (v/v, %/%). | Molar Equiv. | Delivery (min) | Recirculation (min) | Yield (%) |
| --- | --- | --- | --- | --- | --- | --- |
| 1* | 01/481464 | 50/50 | 1.75 | 2.0 | 5.0 | 30.1 |
| 2* | 01/481464 | 50/50 | 1.75 | 5.0 | 6.8 | 38.3 |
| 3* | 01/481464 | 50/50 | 2.38 | 2.7 | 5.0 | 50.5 |
| 4* | 01/481464 | 50/50 | 3.00 | 3.4 | 5.0 | 64.5 |
| 5 | 01/518349 | 50/50 | 2.38 | 2.7 | 5.0 | 78.1 |
| 6* | 01/518349 | 70/30 | 1.75 | 5.0 | 5.0 | 76.0 |
| 7 | 01/518349 | 70/30 | 1.75 | 5.0 | 5.0 | 73.9 |

*Sulfurization step was also modified, using 92.61 mL delivered over 4.6 min.

As illustrated in Table 3, the results demonstrated that the coupling reagent having a higher ratio of activator to phosphoramidite (70/30) was more effective in activating cEt phosphoramidites providing more efficient coupling compared to the standard ratio (50/50). Since the equivalents of cEt amidite used is the same as for standard protocols using other amidites the modified ration of activator to cEt amidite is monetarily advantageous, especially for larger scale syntheses. Using a standard flow rate for delivery of this ratio resulted in an increased delivery time to provide the standard amount of 1.75 equivalents of amidite. Delivery and recirculation provide for 3 full passes of the coupling reagent through the solid support. The delivery and additional activator/CAN (discussed below) are run at a flow rate of 17.5 mL/min. This provides one full pass at full strength for the coupling reagent. The flow rate is then increased to 35.2 mL/min for 2 more passes. The times for delivery and recirculation are calculated based on the volume of the reaction vessel and any other volumes such as recycling plumbing to provide the 3 passes at the two flow rates.

Based on the results obtained for the syntheses illustrated in Table 3, a more efficient coupling protocol for the coupling of cEt amidites is provided (Table 4). These coupling protocols have been adapted for the large scale synthesis of oligomeric compounds on 220 and 600 mmol scale (see Examples 7 and 8). Essentially, for the coupling of cEt amidites improved coupling results from using a coupling reagent having an increased ratio of activator solution to amidite solution. The delivery of the coupling reagent is slower resulting in a longer contact time and a longer recirculation time is also utilized.

Volumes and flow rates are normalized by synthesis scale. 0.2 M cEt phosphoramidite and 1.0 M dicyanoimidazole with 0.1 M N-methylimidazole are delivered simultaneously by two separate pumps at 1.75 mL/min/mmol and 4.10 mL/min/mmol, respectively for a total volume of 29.25 mL/mmol of reagent delivered over 5.0 minutes. Additional activator is pushed simultaneously with ACN at 1.75 mL/min/mmol and 4.10 mL/min/mmol, respectively for a fixed volume of 7.0 mL to ensure that all coupling reagents reach recirculation loop. The coupling reagents are recirculated through the syntheses column at 5.85 mL/min/mmol for 1.8 min and then at 17.60 mL/min/mmol for 3.2 min to afford a total of 3 passes through the synthesis column. The column is then rinsed with 25.28 mL/mmol of ACN at 17.6 mL/min/mmol for 1.4 min.

otides (SEQ ID NO: 02 and SEQ ID NO: 03) were prepared at a 2.0 mmol scale.

As illustrated, the results obtained in Table 5 demonstrated that desirable oligonucleotide yields could be achieved with 1.75 molar equivalents of cEt phosphoramidite using a coupling reagent comprising 70% activator solution and 30% cEt phosphoramidite solution (%/%, v/v).

| SEQ ID NO./ ISIS NO. | Composition (5' to 3') |
|---|---|
| 02/486178 | $A_k{}^{Me}C_kA_k\text{ATAAATA}{}^{Me}C{}^{Me}\text{CGA}_kG_kG_k$ |
| 03/486179 | $A_kG_kA_k{}^{Me}\text{CAATAAATA}{}^{Me}C{}^{Me}C_kG_kA_k$ |

Each internucleoside linkage is a phosphorothioate and each nucleoside not followed by a subscript k is a β-D-2'-deoxyribonucleoside. Each $^{Me}C$ is a 5-methyl cytosine modified nucleoside. Each nucleoside followed by a subscript "k" is a bicyclic nucleoside having a 4'-CH((S)—CH$_3$)—O-2' bridge also referred to as a (S)-cEt modified nucleoside.

TABLE 5 cEt phosphoramidite coupling conditions used for Example 6

| Run | SEQ ID NO./ ISIS NO. | Activator/ amidite | Molar Equiv. | Delivery (min) | Recirculation (min) | Yield (%) |
|---|---|---|---|---|---|---|
| 1 | 02/486178 | 70/30 | 1.75 | 5.0 | 5.0 | 63.1 |
| 2 | 03/486179 | 70/30 | 1.75 | 5.0 | 5.0 | 66.5. |

EXAMPLE 7

Synthesis of Oligonucleotides Comprising cEt Nucleosides (2.2 mmol scale)

The improved protocols illustrated in examples 5 and 6 were further evaluated to determine the effect of lowering the molar equivalents of cEt phosphoramidites in the steps using these amidites and also modifying the recirculation

TABLE 4

Modified cEt phosphoramidite coupling conditions at laboratory-scale

| Synthesis Step | Reagent/Solvent | Volume (mL/mmol) | Flow Rate (mL/mmol/min) | Delivery (min) | Recirculation (min) |
|---|---|---|---|---|---|
| Coupling reagent delivery | activator/cEt solution | 20.50/8.75 | 4.10/1.75 (70/30) | ~5.0 | |
| Coupling reagent push | activator/ACN solution | 7.00 mL (fixed)[1] | 4.10/1.75 (70/30) | ~0.60[2] | |
| Coupling | NA | NA | 5.85/17.60 | | ~1.8/3.2 (5.0 min) |
| Coupling wash | ACN | 25.28 | 17.6 | ~1.4 | |

[1] This volume is dependent on the hold-up volume on the particular synthesizer in use. The volume is intended to push all of the coupling reagents into the recirculation loop.
[2] Delivery of additional activator solution varies with scale. For 2 mmol calculation: 7 mL/[(4.1 + 1.75)] × 2 = 0.60 min.

EXAMPLE 6

Synthesis of Oligonucleotides Comprising cEt Nucleosides (2.0 Mmol Scale)

Using the improved protocols for cEt coupling developed and illustrated in Example 5, two 3/10/3 gapped oligonucletimes. A 3/10/3 gapped oligonucleotide (SEQ ID NO: 01, ISIS No. 481464, see Example 5) was prepared at a 2.2 mmol scale using the protocols illustrated in examples 5 and 6 using the molar equivalents of cEt phosphoramidites and recirculation times presented in Table 6. The ration of activator to cEt amidite is 70/30 with reduced volumes being used to lower the molar equivalents of cEt amidite delivered.

TABLE 6 cEt phosphoramidite coupling/recirculation conditions used for Example 7

| Molar Equiv. | Recirculation (min) | Relative Yield (%) |
|---|---|---|
| 1.75 | 10.0 | −0.3 |
| 1.75 | 7.5 | 0.8 |
| 1.75 | 5.0 | 0.0 (Control) |
| 1.5 | 10.0 | −1.0 |
| 1.5 | 7.5 | 5.9 |
| 1.5 | 5.0 | −0.5 |
| 1.4 | 10.0 | 4.5 |
| 1.4 | 7.5 | 3.1 |
| 1.4 | 5.0 | −0.9 |
| 1.3 | 10.0 | −0.9 |
| 1.3 | 7.5 | −3.4 |
| 1.3 | 5.0 | −8.9 |

Reducing the molar equivalents of cEt phosphoramidite and adjusting the recirculation times can provide an increased yield as shown in Table 6. Furthermore reduction of the cEt equivalents to as low as 1.3 equivalents and increasing the cEt recirculation time up to 10 minutes had a negligible effect on the total impurity profile.

EXAMPLE 8

Synthesis of Oligonucleotides Comprising cEt Nucleosides (220 Mmol Scale)

Synthesis of ISIS 481464 (SEQ ID NO: 01) as illustrated in Example 5 was performed on a 220 mmol scale following standard oligonucleotide synthesis protocols with modified coupling protocols used for cEt amidites. The synthesis was performed on an OligoProcess synthesizer skid (GE Healthcare). To accommodate the change in equipment and improve process robustness, the optimized cEt coupling conditions were slightly modified from that described in Example 5 and is presented in Table 7. The cEt coupling reagent delivery was decreased slightly from 5.0 min to 4.7 min; the coupling push step was adjusted from 7.0 mL to 1.0 L; the first recirculation time was adjusted from 1.8 min to 2.7 min, and the phosphorus deprotection recirculation time was reduced from 120 min to 30 min.

As illustrated in Table 8, modification of the ratio of the activator solution to the phosphoramidite solution from the standard 50/50 to 70/30 (%/%, v/v) and delivering the same 1.75 molar equivalents of cEt phosphoramidite as with standard protocols resulted in a more efficient synthesis.

TABLE 8

Modified cEt phosphoramidite coupling conditions

| Synthesis Step | Reagent/Solvent | Volume (mL/mmol) | Flow Rate (mL/mmol/min) | Delivery or Recirculation time (min) |
|---|---|---|---|---|
| coupling reagent | activator (70%) | 20.38 | 4.38 | 4.7 |
| | cEt amidite (30%) | 8.74 | 1.87 | |
| reagent push | activator (70%) | 1.0 L (fixed)[1] | 4.38 | 0.73 |
| | ACN (30%) | | 1.87 | |
| recirculation | NA | NA | 6.25 then 17.60 | 2.7 then 2.3 (total 5.0) |
| Coupling wash | ACN | 25.28 | 17.6 | 1.4 |

[1]This volume is dependent on the hold-up volume on the particular synthesizer in use. The volume is intended to push all of the coupling reagents into the recirculation loop. The yield for ISIS 481464 (SEQ ID NO: 01) was 80.2%.

EXAMPLE 9

Synthesis of Oligonucleotides Comprising cEt Nucleosides (600/900 Mmol Scale)

Synthesis of ISIS 481464 (SEQ ID NO: 01) as illustrated in Example 5 was performed on a 600 mmol scale following standard oligonucleotide synthesis protocols with modified coupling protocols for cEt amidites as illustrated in Example 8. The synthesis was performed on an OligoProcess synthesizer skid (GE Healthcare). The standard protocols were also modified such that the phosphorus deprotection recirculation time was 60 min.

As illustrated in Example 8, modification of the ratio of the activator solution to the phosphoramidite solution from the standard 50/50 to 70/30 (%/%, v/v) and delivering the same 1.75 molar equivalents of cEt phosphoramidite as with standard protocols resulted in a more efficient synthesis. The results are consistent with those obtained in examples 5, 6 and 8, providing a yield of 66.6% for ISIS 481464 (SEQ ID NO: 01).

The synthesis was also performed on 900 mmol scale with comparable results.

EXAMPLE 10

General Procedure for analyzing a Crude Sample After Cleavage From Solid Support Analysis of a crude, DMT-on product is conducted by Ion-pair reverse phased High Performance Liquid Chromatography with Ultraviolet detection coupled to Mass Spec-

TABLE 7

Standard oligonucleotide synthesis protocol (220 mmol)

| Synthesis Step | Cycle | Volume (mL/mmol) | Flow Rate (mL/min/mmol) | Delivery (min) | Recirculation (min) |
|---|---|---|---|---|---|
| Detritylation | 1 (Uny) | 89.14 | 23.14 | 3.85 | |
| | 2-16 | 63.68 | 23.14 | 2.75 | |
| Coupling (cEt) | 1-3 14-16 | (see Table 7 for cEt coupling conditions) | | | |
| Coupling (deoxy) | 4-13 | 17.50 | 8.73[1] | 2.0 | 3.0[3] |
| Sulfurization | 1-16 | 32.41 | 10.14 | 3.2 | |
| Capping (Reagent A/B) | 1 (Uny) | 81.05 | 10.82[2] | 7.5 | 7.5[4] |
| | 2-15 | 16.18 | 10.82[2] | 1.5 | |
| Phosphorus Deprotection | NA | 46.32 | 23.14 | 2.0 | 30.10 |

[1]Deoxy phosphoramidite and activator solutions were delivered simultaneously, 50/50, %/% (v/v)
[2]Capping A and capping B solutions were delivered simultaneously, 50/50, %/% (v/v)
[3]Following delivery, reagents were recirculated at 8.8 mL/min/mmol for 1.2 min. and 17.6 mL/min/mmol for 1.8 min.
[4]Following delivery, reagents were recirculated at 17.6 mL/min/mmol for 7.5 min.

trometry (IP-HPLC-UV-MS) using Agilent 1100 Series and Water's XBridge C18 3.5 µM column (2.1 mm×150 mm) with part number 186003023. Mobile Phase A comprises J.T. Baker Water with 10% acetonitrile, 5 mM TBuAA (tributylammonium acetate), and 1 µM EDTA (ethylenediaminetetraacetic acid). Mobile Phase B comprises J.T. Baker Water with 80% acetonitrile, 5 mM TBuAA and 1 µM EDTA.

IP-HPLC-UV-MS methods are used to analyze the crude, DMT-on product after cleavage from a support medium. The general gradient conditions are shown below.

The impurity profile of oligonucleotides is determined by IP-HPLC-UV-MS. It is not possible to resolve all of the impurities from the parent oligonucleotide by IP-HPLC-UV; therefore all components that elute within the main UV peak are quantified by mass spectrometry. This is accomplished by extracting the ion currents due to all components that elute within the main UV peak. Taking average mass spectrum under the main UV peak gives an overview of the mass spectral dimension of the impurity profile at a glance. Overlay of average mass spectra from control and experimental samples provides an overall picture of the shift in impurities eluting under the main UV peak.

SEQUENCE LISTING

<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1
ctatttggat gtcagc                                                 16

<210> SEQ ID NO 2
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 2
acaataaata ccgagg                                                 16

<210> SEQ ID NO 3
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 3
agacaataaa taccga                                                 16

| Time (min) | Mobile Phase A (%) | Mobile Phase B (%) | Flow Rate (mL/min/mmol) |
|---|---|---|---|
| 0.00 | 55.00 | 45.00 | 0.250 |
| 22.00 | 20.00 | 80.00 | 0.250 |
| 30.00 | 20.00 | 80.00 | 0.250 |
| 31.00 | 55.00 | 45.00 | 0.250. |

IP-HPLC-UV-MS analysis

Add a sample of crude solution to a tared centrifuge tube, record sample mass, vacuum centrifuge at ambient temperature to dryness, and reconstitute in a known mass of 0.01% TEA in water. Generally, 25 mg of crude is reconstituted in 2000 mg of 0.01% TEA. An appropriate concentration of 2.5 $AU_{260}$/mL is generally an appropriate goal for the dilution. Analyze the crude sample by IP-HPLC-UV-MS to determine purity and yield.

What is claimed is:

1. A method of coupling solid support bound free hydroxyl groups to bicyclic nucleosides of Formula I:

wherein for each bicyclic nucleoside of Formula I:
  Bx is an optionally protected heterocyclic base moiety;
  $T_1$ is a hydroxyl protecting group;
  $T_2$ is a reactive phosphorus group capable of forming an internucleoside linkage;
  one of $Q_1$ and $Q_2$ is H and the other of $Q_1$ and $Q_2$ is $C_1$-$C_6$ alkyl or substituted $C_1$-$C_6$ alkyl where each substituted group is $OJ_1$, $SJ_1$, $NJ_1J_2$, $N_3$ or CN wherein each $J_1$ and $J_2$ is, independently, H or $C_1$-$C_6$ alkyl;

comprising treatment of the free hydroxyl groups with a coupling reagent which is about 70% by volume activator solution consisting of 1.0 molar 4,5-dicyanoimidazole and about 0.1 molar N-methylimidazole in acetonitrile and about 30% by volume of a solution having about a 0.2 molar concentration of bicyclic nucleosides of Formula I disolved in acetonitrile or a mixture of acetonitrile and toluene and wherein the volume of coupling reagent added provides about 1.75 equivalents of bicyclic nucleosides of Formula I based on the initial loading of the solid support with free hydroxyl groups.

2. The method of claim 1 wherein the initial loading of the free hydroxyl groups on the solid support is greater than about 100 mmol.

3. The method of claim 1 wherein the initial loading of the free hydroxyl groups on the solid support is greater than about 200 mmol.

4. The method of claim 1 wherein the initial loading of the free hydroxyl groups on the solid support is from about 220 mmol to about 900 mmol.

5. The method of claim 1 wherein the initial loading of the free hydroxyl groups on the solid support is greater than about 200 mmol and the delivery of the coupling reagent to the solid support is at a flow rate that requires from about 4 to about 5 minutes to deliver the about 1.75 equivalents.

6. The method of claim 5 further comprising recirculation of the coupling reagent for a time of from about 4.5 to about 5.5 minutes.

7. The method of claim 1 wherein the free hydroxyl groups are bound to the solid support through linking moieties.

8. The method of claim 1 wherein each of the free hydroxyl groups are provided by solid support bound UNYLINKER™ groups having one of the formulas:

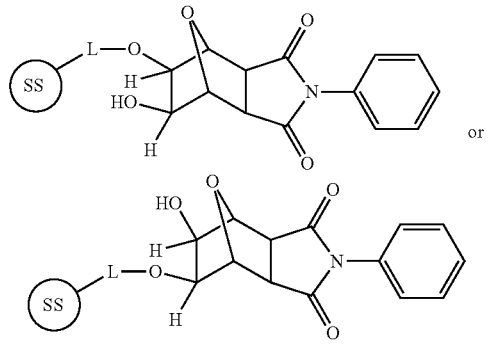

wherein L is a linking moiety and SS is a solid support.

9. The method of claim 1 wherein each reactive phosphorus group is a diisopropylcyanoethoxy phosphoramidite.

10. The method of claim 1 wherein each $T_1$ is 4,4'-dimethoxy-trityl.

11. The method of claim 1 wherein one of $Q_1$ and $Q_2$ is H and the other of $Q_1$ and $Q_2$ is $CH_3$.

12. The method of claim 1 wherein each heterocyclic base moiety is, independently, uracil, thymine, cytosine, 4-N-benzoylcytosine, 4-N-benzoyl-5-methyl-cytosine, adenine, 6-N-benzoyladenine, guanine or 2-N-isobutyrylguanine.

13. The method of claim 1 wherein dichloroacetic acid in toluene is used to deblock blocked hydroxyl groups.

14. The method of claim 13 further comprising treatment with triethylamine in acetonitrile to remove phosphorus protecting groups thereby providing linkages between monomer subunits that are independently selected from phosphodiester and phosphorothioate.

15. The method of claim 14 further comprising treatment with ammonium hydroxide to remove further protecting groups and cleave the oligomeric compound from the solid support.

* * * * *